(12) United States Patent
Olson

(10) Patent No.: US 6,546,286 B2
(45) Date of Patent: Apr. 8, 2003

(54) BATTERY-LESS, HUMAN-POWERED ELECTROTHERAPY DEVICE

(75) Inventor: Renee C. Olson, Hudson, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/793,092

(22) Filed: Feb. 27, 2001

(65) Prior Publication Data

US 2002/0120295 A1 Aug. 29, 2002

(51) Int. Cl.[7] ................................................. A61N 1/39
(52) U.S. Cl. ................................. 607/5; 607/2; 607/61
(58) Field of Search .............................. 607/2, 4, 5, 9, 607/10, 37, 61

(56) References Cited

U.S. PATENT DOCUMENTS

| | | | | |
|---|---|---|---|---|
| 3,456,134 A | * | 7/1969 | Ko | 310/319 |
| 3,563,245 A | * | 2/1971 | McLean et al. | 607/35 |
| 3,659,615 A | * | 5/1972 | Enger | 174/52.4 |
| 3,693,625 A | * | 9/1972 | Auphan | 607/19 |
| 4,088,949 A | | 5/1978 | Goldish et al. | |
| 4,453,537 A | * | 6/1984 | Spitzer | 600/17 |
| 4,524,437 A | | 6/1985 | Koike | |
| 4,669,007 A | | 5/1987 | Fujishige | |
| 5,318,501 A | * | 6/1994 | Lee et al. | 600/16 |
| 5,496,356 A | * | 3/1996 | Hudz | 463/47.3 |
| 5,593,427 A | | 1/1997 | Gliner et al. | |
| 5,607,454 A | | 3/1997 | Cameron et al. | |
| 5,735,879 A | | 4/1998 | Gliner et al. | |
| 5,800,504 A | * | 9/1998 | Bellifemine | 607/115 |
| 5,836,993 A | | 11/1998 | Cole | |
| 5,879,374 A | | 3/1999 | Powers et al. | |
| 5,982,577 A | | 11/1999 | Brown et al. | |

FOREIGN PATENT DOCUMENTS

| | | |
|---|---|---|
| GB | 2 262 324 | 6/1993 |
| WO | WO94/27674 | 12/1994 |

* cited by examiner

Primary Examiner—Kennedy Schaetzle

(57) ABSTRACT

An electrotherapy device including a human powered power supply. An energy delivery system is operably connected to the power supply for delivering an electric energy to a patient. A controller is operably connected to the energy delivery system for controlling the energy delivery system.

18 Claims, 4 Drawing Sheets

BATTERY-LESS, HUMAN-POWERED ELECTROTHERAPY DEVICE

BACKGROUND OF THE INVENTION

1. Field of the Invention

The present invention relates generally to an electrotherapy device. Specifically, the present invention relates to an electrotherapy device that is manually powered. More specifically, the present invention relates to a battery-less, human-powered electrotherapy device and method of use. Electrotherapy devices include defibrillators, cardioverters and training devices that simulate the operation of an electrotherapy device. Defibrillators include automatic or semi-automatic external defibrillators (AEDs); including those defibrillator that deliver monophasic, biphasic or multiphasic waveforms externally to a patient.

2. Description of the Prior Art

Electrotherapy devices are used to provide electric shocks to treat patients for a variety of heart arrhythmias. For example, external defibrillators typically provide relatively high-energy shocks to a patient (as compared to implantable defibrillators), usually through electrodes attached to the patient's torso. External defibrillators are used to convert ventricular fibrillation ("VF") or shockable ventricular tachycardia ("VT") to a normal sinus rhythm. Similarly, external cardioverters can be used to provide paced shocks to convert atrial fibrillation ("AF") to a more normal heart rhythm.

Sudden cardiac arrest ("SCA") is the leading cause of unanticipated death in the United States. On average, about 600 people per day die of SCA. This translates to nearly one death every two minutes. It is likely that these statistics would hold true for third world countries. Precise international statistics are not available but the U.S. rate for coronary heart disease deaths, of which sudden deaths constitute nearly half, is representative of international rates (rank 16$^{th}$ and 13$^{th}$ among 36 nations reported by the World Health Organization (WHO), for men and women, respectively).

Most sudden cardiac death is caused by VF, in which the heart's muscle fibers contract without coordination, thereby interrupting normal blood flow to the body. The only effective treatment for VF is electrical defibrillation, which applies an electrical shock to the patient's heart. The electrical shock clears the heart of the abnormal electrical activity (in a process called "defibrillation") by depolarizing a critical mass of myocardial cells to allow spontaneous organized myocardial depolarization to resume.

To be effective, the defibrillation shock must be delivered to the patient within minutes of the onset of VF. Studies have shown that defibrillation shocks delivered within one minute after the onset of VF achieve up to a 100% survival rate. However, the survival rate falls to approximately 30% after only 6 minutes. Beyond 12 minutes, the survival rate approaches zero. Importantly, the more time that passes, the longer the brain is deprived of oxygen and the more likely that brain damage will result. As improved access to defibrillators increases, survival rates from SCA also increase.

The electrical pulse must be delivered within a short time after onset of VF in order for the patient to have any reasonable chance of survival. To be effective, the defibrillation shock must be delivered to the patient within minutes of the onset of VF. Studies have shown that defibrillation shocks delivered within one minute after the onset of VF achieve up to a 100% survival rate. However, the survival rate falls to approximately 30% after only 6 minutes. Beyond 12 minutes, the survival rate approaches zero. Importantly, the more time that passes, the longer the brain is deprived of oxygen and the more likely that brain damage will result. Electrical fibrillation may also be used to treat shockable ventricular tachycardia ("VT"). Accordingly, defibrillation is the appropriate therapy for any shockable rhythm, that is, VF or shockable VT.

One way of providing electrical defibrillation uses implantable defibrillators, which are surgically implanted in patients that have a high likelihood of experiencing VF. Implanted defibrillators typically monitor the patient's heart activity and automatically supply the requisite electrical defibrillation pulses to terminate VF. Implantable defibrillators are expensive, and are used in only a small fraction of the total population at risk for sudden cardiac death.

External defibrillators send electrical pulses to a patient's heart through electrodes applied to the patient's torso. External defibrillators are typically located and used in hospital emergency rooms, operating rooms, and emergency medical vehicles. Of the wide variety of external defibrillators currently available, automatic and semi-automatic external defibrillators, collectively referred to as "AEDs", are becoming increasingly popular because relatively inexperienced personnel can use them. U.S. Pat. No. 5,607,454 to Cameron et al., entitled Electrotherapy Method and Apparatus, and PCT publication number WO 94/27674, entitled Defibrillator With Self-Test Features, the specifications of which are hereby incorporated by reference, describe AEDs.

AEDs provide a number of advantages, including the availability of external defibrillation at locations where external defibrillation is not regularly expected, and is likely to be performed quite infrequently, such as in residences, public buildings, businesses, personal vehicles, public transportation vehicles, among other locations A big problem with deploying a device, such as a defibrillator, in a remote location is the need to ensure a reliable power supply. Because of the cost, disposable batteries are not a practical solution. Additionally, because of the lack of an AC or DC power supply generally, rechargeable batteries are also not a practical solution. What is needed, therefore, is a device that is capable of monitoring a patient and defibrillating the patient's heart, if necessary, but which can be powered manually.

SUMMARY OF THE INVENTION

The present invention provides an electrotherapy device including a human powered power supply. An energy delivery system is operably connected to the power supply for delivering an electric energy to a patient. A controller is operably connected to the energy delivery system for controlling the energy delivery system.

The present invention also provides a method for operating a defibrillator. A human powered power supply is operated. It is determined whether a patient has a shockable rhythm. A defibrillating shock is administered to the patient through an energy delivery system operably connected to the human powered power supply if the patient has a shockable rhythm Still other objects and advantages of the present invention will become readily apparent by those skilled in the art from a review of the following detailed description. The detailed description shows and describes preferred embodiments of the invention, simply by way of illustration of the best mode contemplated of carrying out the present invention. As will be realized, the invention is capable of other and different embodiments and its several details are capable of modifications in various obvious respects, without departing from the invention. Accordingly, the drawings and description are illustrative in nature and not restrictive.

BRIEF DESCRIPTION OF THE DRAWINGS

Objects and advantages of the present invention will be more clearly understood when considered in conjunction with the accompanying drawings, in which.

DESCRIPTION OF THE PREFERRED EMBODIMENTS

The following discussion is presented to enable a person skilled in the art to make and use the invention. Various modifications to the preferred embodiment will be readily apparent to those skilled in the art, and the generic principles herein may be applied to other embodiments and applications without departing from the spirit and scope of the present invention as defined by the appended claims. Thus, the present invention is not intended to be limited to the embodiment shown, but is to be accorded the widest scope consistent with the principles and features disclosed herein.

Figure 1:
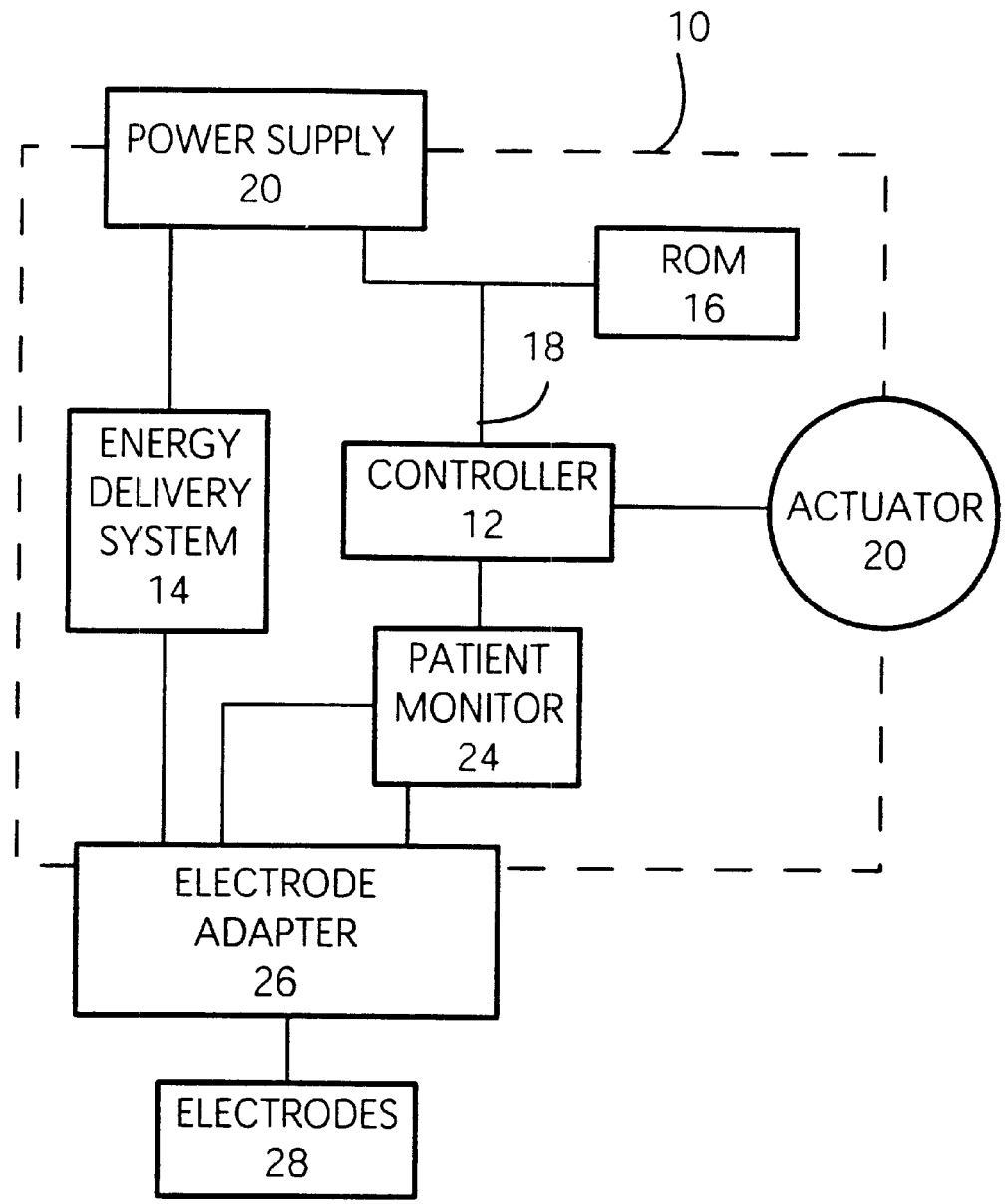
FIG. 1 represents a block diagram of an electrotherapy device showing a detachable electrode system.

FIG. 1 is a block diagram showing an electrotherapy device 10. The device 10 may include the ability to defibrillate, cardiovert, or pace a patient, or a combination of these functions. Device 10 can include a controller 12 for operating an energy delivery system 14 and for performing other aspects of the operation of the device. Software instructions for the operation of the device may be accessible from a memory device. For example, software may be stored in read only memory (ROM), such as incorporated ROM 16. Any other memory structure, such as RAM or other memory device may also be utilized. The controller may access instructions for operation from ROM 16. It should be understood that in this and other embodiments described below "controller" means a microprocessor, controller, gate array, other control logic, or any combination of these elements.

Controller 12 can communicate with ROM 16 via a memory bus 18. A recordable memory module 32 may be attached to device 10 via an electrode system 36, as shown in FIG. 1. Electrode system 36 can include electrodes 28 and an electrode adapter 26.

Electrode adapter 26 may be connected to electrodes 28 and may be removably connected to the device 10. A suitable electrode system 36 adaptable for use in this invention would be, for example, Heartstream ForeRunner® electrodes.

Electrodes 28 can communicate with a patient monitor 24 via an electrode adapter 26 to provide patient ECG data from the patient to the patient monitor 24. The electrodes include electrodes capable of delivering defibrillation, monitoring a patient condition, delivering pacing pulses, or a combination of those features. In an AED, the patient monitor 24 can monitor the patient for a heart rhythm and subsequently determine whether the monitored rhythm is shockable.

When a shockable rhythm is detected, the patient monitor 24 can then communicate a shock decision to the controller 12. Next, the controller 12 can communicate to the energy delivery system 14. Subsequently, the energy delivery system 14 can deliver a therapeutic energy pulse to the patient (not shown) through electrodes 28 attached to the defibrillator 10 via electrode adapter 26, using the power supply 20 as the energy source.

The power supply typically is physically separate from the defibrillator. Such a construction permits the defibrillator to be placed near a patient in need of treatment to permit proper attachment of treatment electrodes and access by a user. On the other hand, the power supply could be arranged in a location suitable for actuation by a person. The power supply could be actuated by hand, or typically by foot action. Typically, it would be desirable to maintain a separation between the power supply and attached electrotherapy device and/or the patient, if possible. This can help to ensure that the operator of the power supply has adequate space to effectively operate the power supply. Along these lines, the power supply may be oriented as desired or necessary to facilitate its operation. Also, the physical separation of the power supply and the electrotherapy device and/or patient could help to avoid damage to the electrotherapy device and injury to the patient as the power supply is vigorously actuated.

An electrical cable could connect the defibrillator and the power supply. The cable could be permanently attached to the defibrillator and/or the power supply. Alternatively, the cable could be detachably connected to either the defibrillator and/or the power supply.

The power supply can include a human-actuatable member. One example of a human actuatable member is a foot pump including an opposing spring. By including a foot pedal with an opposing spring, the person powering the device may do so from a convenient standing position. This permits the person to utilize the large and powerful muscle groups in the leg and work in the direction of gravity. Any other human actuatable member could also be utilized, such as a hand-operated member. More than one human actuatable member could accelerate the process of power generation.

The human actuatable member may be connected to a shaft. A gear system, such as a ratcheted gear system, may connect the human actuatable member to the shaft. The gear system may be constructed to provide a constant rotational direction to the shaft.

The shaft may be connected to a generator. Typically, the generator is a DC generator or dynamo. One particular embodiment utilizes a commercially available three-phase permanent magnet alternator including internal rectifier diodes. By providing constant rotation of the shaft, magnets in a DC generator would be constantly rotated.

Rather than the human actuatable member being connected directly or indirectly to a generator as described above, it could be connected directly or indirectly to a watch-type spring, which uncoils to release its energy. Such an embodiment could include a human actuatable member that winds the spring. For example, a hand-actuated crank could be utilized to wind up the spring.

Energy generated by the human actuatable elements may be stored for use in operating the defibrillator. Any means for storing power may be utilized. For example, one or more batteries may be utilized to store the power. The battery(ies) could be recharged by the human actuatable members. Also, a capacitor, such as a "super capacitor" could be utilized to store the energy.

"Super capacitors" or large capacitance capacitors, that is, capacitors of the multiple farad electrical size, are also known as double-layer capacitors in the art. Such "super capacitors" may replace batteries for energy storage uses for reasons of size, weight, reliability and decreased maintenance requirements, and are now readily available as commercial products. Capacitors of this nature are, however, most readily fabricated as units of large electrical size having moderate operating voltage capability. As noted below herein, sizes, such as an integral number of farads of electrical capacitance and a few tens of operating volts capability, are now conveniently provided. Capacitors of this electrical rating may of course be combined in appropriate series and parallel combinations.

By way of additional background, Helmholtz first investigated the super capacitor element in 1879. According to one super capacitor arrangement, one electrode of the device is made of carbon and the other is made of a liquid electrolyte. When a voltage is applied to the carbon layer with respect to the liquid electrolyte, a thin dielectric layer is established adjacent the carbon layer particles. The effective surface area of the dielectric layer and the carbon particles is, however, extremely large. Surface areas on the order of about 1000 square meters per gram of carbon material can be achieved with such electrode arrangements because of the porous surface of the carbon and the small carbon particle size. The thickness of the dielectric layer on the other hand can be extremely small, such as on the order of about 1 nanometer. As a result, a high ratio of surface area to dielectric thickness can be obtained and surprising capacitances per unit of capacitor volume are obtainable, therefore desirable volumetric efficiency is obtained for such a capacitor. As may be surmised from a consideration of such structural details, however, questions of permissible operating voltage, that is, the dielectric strength of the thin dielectric layer, tolerable current flow rates and resulting temperature Arise, energy losses, liquid electrolyte inconvenience and physical stability of this type of super capacitor require special consideration in the capacitor's design and fabrication sequences.

The large capacitance of super capacitors nevertheless permits the storage of relatively large amounts of energy. Presently available super capacitors are capable of several hundred farads of capacitance within a single physical container and with an operating voltage of 3–20 volts. Such capacitors provide a stored energy density of 10–20 joules per gram of capacitor weight.

One particular example of super capacitors that could be utilized according to the present invention are "Powercache" super capacitors available from Maxwell Technologies. Information about these particular super capacitors is available at www.powercache.com, the entire contents of which and any link sites are hereby incorporated by reference. Any other suitable super capacitor may also be utilized.

According to one embodiment, it is desired that the power supply be capable of operating for about 10 minutes and supply a single shock to a patient as a low energy biphasic. To operate in these parameters, requires the system to produce about 1700 J. The amount of energy required for the system to produce should take into account inefficiencies of generators, the speed with which it is required to energy be released, the desired therapy to be administered to a patient, as well as other factors.

A device according to the present invention may have two operational states. In one state, the device will monitor the patient. Low energy drain is associated with this state. On the other hand, in a second state, the device will be able to deliver a therapeutic shock to a patient. This is a high energy drain state.

A typical healthy human can sustainably generate about 125 watts and up to about 1500 watts in short bursts. Therefore, approximately 20 seconds of pumping would be sufficient to generate the energy required for one shock, the minimum necessary and about 10 minutes of monitoring. This is based upon needing about 1700 J for the system and an efficiency of the system of about seventy percent, and a resulting need of about 2500 J input. The also assumes that an average person using a foot-pedal crank, similar to that on a bicycle, can generate about 125 watts sustainably. Since 1 watt=1 J/sec, 20 seconds would be needed in such a case to generate the required power.

According to another view, the maximum power generated from a single vigorous jump or lift is approx. 4500 watts (from Journal of Chemical Education 55: 456–458, 1978). Assume a "normal" jump produces more like half, or 2250 watts. Therefore three jumps, or 5 seconds of vigorous "pumping" should be sufficient.

Of course, the amount of power generated by a person in a period of time may vary not only depending upon the person, but also upon the embodiment. Therefore, the number of seconds that a person needs to pump may vary. During or after the monitoring period, if an additional shock is required or more monitoring is desired, the user may pump the device again.

Figure 3:
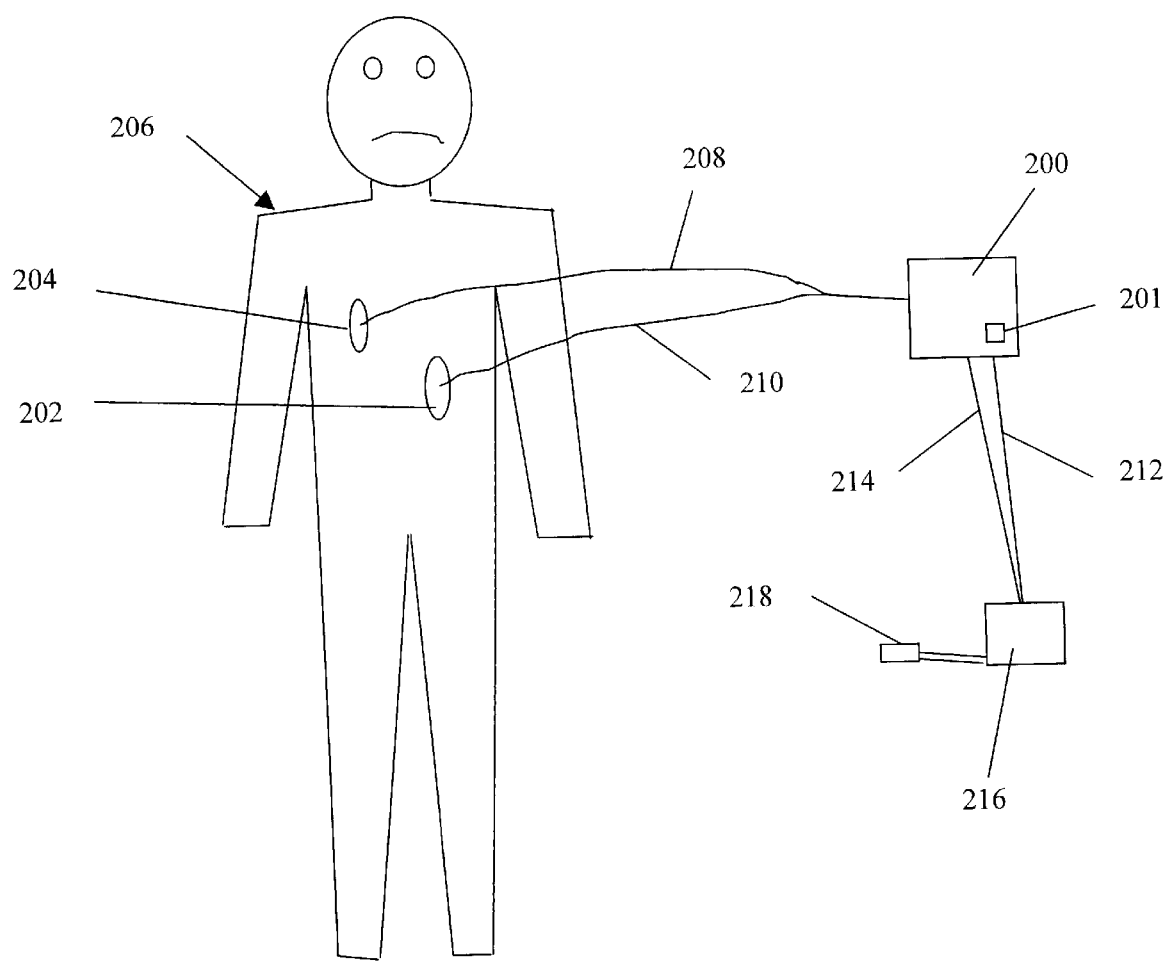
FIG. 3 represents a simple diagram of an embodiment of a device according to the present invention.

Typically, about 5 to about 20 seconds of pumping is needed, depending upon how vigorous the pumping is. More typically, about 10 to about 20 seconds of pumping is required. Typically, a device according to the present invention will include an indicator to indicate when the device is ready to deliver a defibrillating charge. The indicator could be a light producing element, such as one or more lights or LEDs. Also, a display capable of displaying text or any other indicator could be used. FIG. 3 illustrates an indicator 201 on the defibrillator.

Figure 2:
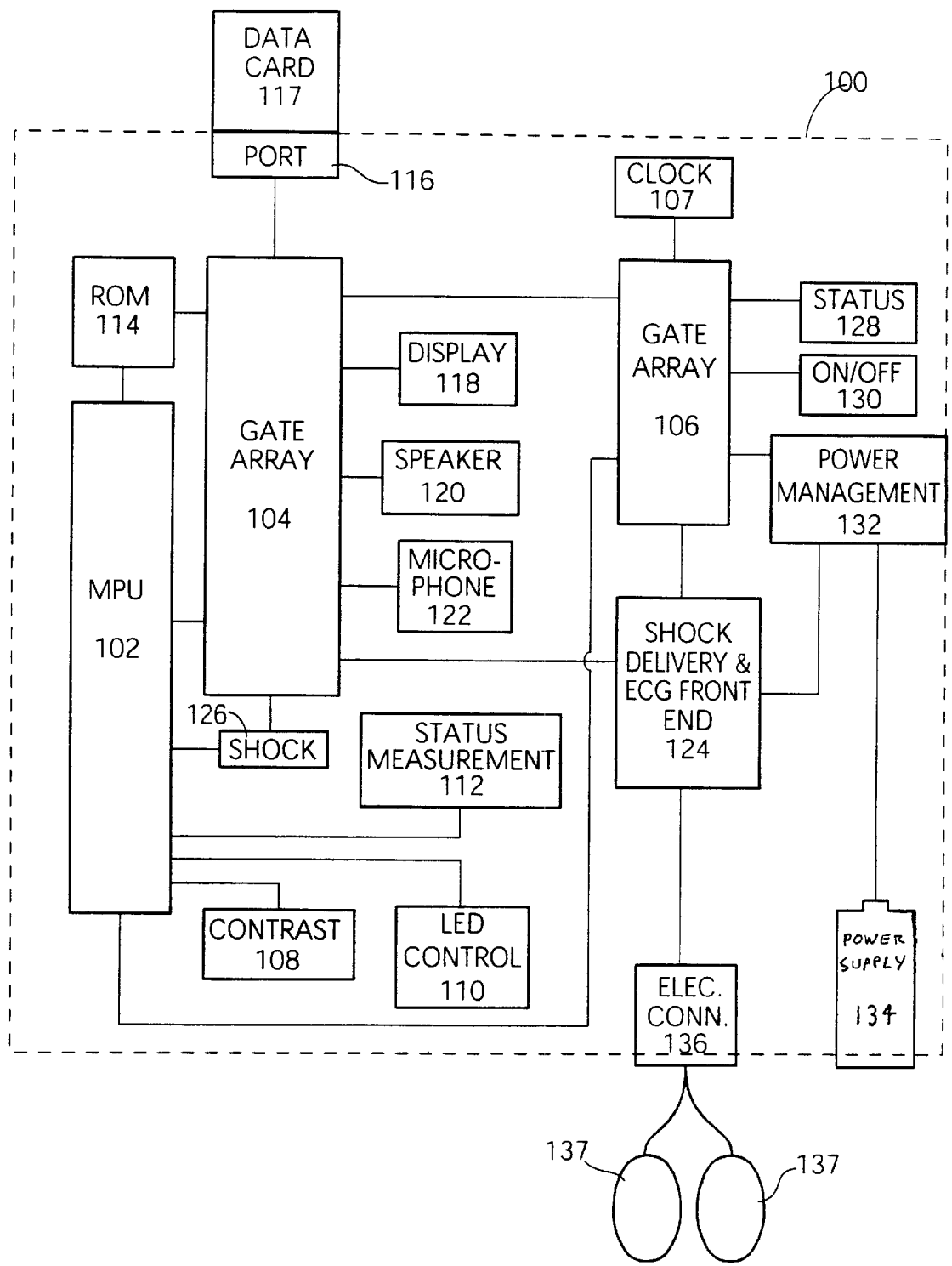
FIG. 2 represents a block diagram that illustrates major components of a semi-automatic external defibrillator shown in FIG. 1.

FIG. 2 represents a block diagram that shows major components of an AED. Further detailed information about the operation of an AED can be obtained in U.S. Pat. No. 5,836,993, to Cole, for "Electrotherapy Device Control System and Method"; and U.S. Pat. No. 5,593,427, to Gliner et al., for "Electrotherapy Method", the specifications of which are incorporated herein by reference. As will be appreciated by those of skill in the art, the invention can be used in a variety of AEDs and is not limited to this configuration, which is used for illustration purposes only.

In the device shown in FIG. 2, defibrillator control functions are divided among a microprocessor unit (MPU) 102 and two custom gate arrays 104 and 106. MPU 102 performs program steps according to software instructions provided to it from ROM 114. Also, MPU 102 controls the operation of certain buttons (such as display contrast buttons 108) and certain system LED's 110 (such as LED's associated with the shock button and the electrode connector). Additionally, MPU 102 also receives system status information as shown by block 112.

The device may include a gate array 104 for implementing the memory map to system ROM 114. System ROM 114 is preferably flash ROM, although EPROM or any other electrically erasable and programmable nonvolatile memory could be used. Gate array 104 also controls a display 118, a speaker 120, and a microphone 122. Gate array 104 can actuate a relay within the shock delivery and ECG front-end system 124 in response to actuation of a shock button 126 by a user during treatment mode.

Gate array 106 can provide a system monitor function by performing automatic self-tests of the defibrillator and its components. Also, the gate array 106 can display the operational status of the defibrillator on a status display 128. Details of suitable self-tests may be found in U.S. Pat. No. 5,879,374, to Powers et al., for "External Defibrillator with Automated Self-Testing Prior to Use", the specification of which is incorporated herein by reference.

In addition to the above, gate array 106 may also act as the defibrillator's interface by including a user-activated on/off switch 130. Furthermore, gate array 106 can control the power management subsystem 132 to provide power to operate system components from power supply 134 and to provide energy to the shock delivery system's capacitor(s) for a therapeutic shock during treatment mode. Still further, gate array 106 may interface with the defibrillator's ECG front end and enable the shock delivery system to deliver a shock in response to detection of a patient ECG pattern requiring treatment (and actuation of the shock button). Also, gate array 106 may control delivery of the shock to electrode connector 136 in response to shock delivery status information obtained during delivery of the shock. Further information regarding this last function may be found in U.S. Pat. No. 5,735,879, to Gliner et al., for "Electrotherapy Method for External Defibrillators"; and U.S. Pat. No. 5,607,454, to Cameron et al., for "Electrotherapy Method and Apparatus"; the specifications of both which are incorporated herein by reference.

These defibrillator components communicate with each other over suitable communication buses, as shown.

External defibrillator 100 can be operated in different modes, such as self-test mode, stand-by mode, set-up mode, patient treatment mode, training mode and code-transfer mode. The operational characteristics of defibrillator 100 differ in each mode. Additionally, the operational characteristics of the defibrillator in any one of the modes can be changed as described below in greater detail.

Operation of the external defibrillator of the embodiment shown in FIG. 2 commences with the insertion of a power supply 134 or user activation of the power on button. Once gate array 106 confirms that a power supply 134 is inserted, gate array 104 may prompt MPU 102 to begin its boot sequence. The boot sequence can begin with MPU 102 sending out a series of addresses to power supply 134.

As is known in the art, while in patient treatment mode, a defibrillator, such as defibrillator 100, typically performs the following functions:

(1) determine whether electrodes 137 are attached to electrode connector 136;

(2) receive ECG information from a patient through such electrodes;

(3) analyze the ECG information to determine whether a therapeutic shock is advised; and (4) deliver a shock to the patient through the electrodes 137 if a shock is advised and if the shock button 126 is actuated by a user.

FIG. 3 illustrates elements of an embodiment of a system according to the present invention. This embodiment includes a defibrillator 200. Two electrodes 202 and 204 attached to patient 206 are connected to the defibrillator through leads 208 and 210. The defibrillator 200 is connected by a pair of leads 212 and 214 to a foot driven power source 216 that includes an embodiment of a foot pedal 218.

Figure 4:
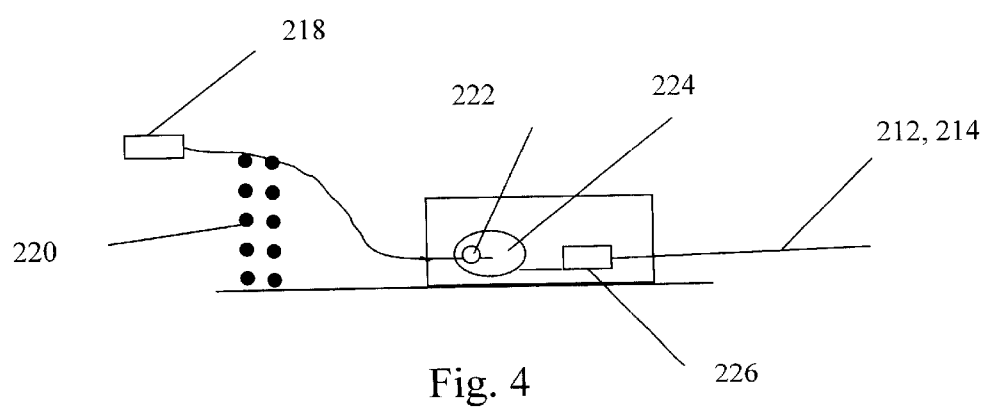
FIG. 4 represents a cross-sectional view of an embodiment of a foot-actuated human powered power supply according to the present invention.

FIG. 4 illustrates the embodiment of a foot driven power source shown in FIG. 3 in greater detail. A foot pedal 218 is biased upward by coil spring 220. Any other suitable spring, such as a leaf spring may also be utilized. The foot pedal 218 drives a shaft 222 that drives a DC generator 224. The foot pedal, shaft, and DC generator are operably connected so as to ensure constant rotational direction in spite of the reciprocating nature of the movement of the foot pedal. A super capacitor 226 could store the energy for release to the defibrillator to administer electrotherapy to the patient. Leads or cables 212 and 214 connect the power source to the defibrillator.

The amount of power required to perform a particular electrotherapy on a patient is known in the art. Also, the amount of power that a manually operated generator requires is also known. For example, a hand powered radio is available from Baygen Power Industries Limited, of Cape Town, South Africa. Hand powered flashlights are also known. Therefore, those of ordinary skill in the art would be able to devise a manually operated power supply to satisfy the requirements of electrotherapy devices without undue experimentation.

Figure 5:
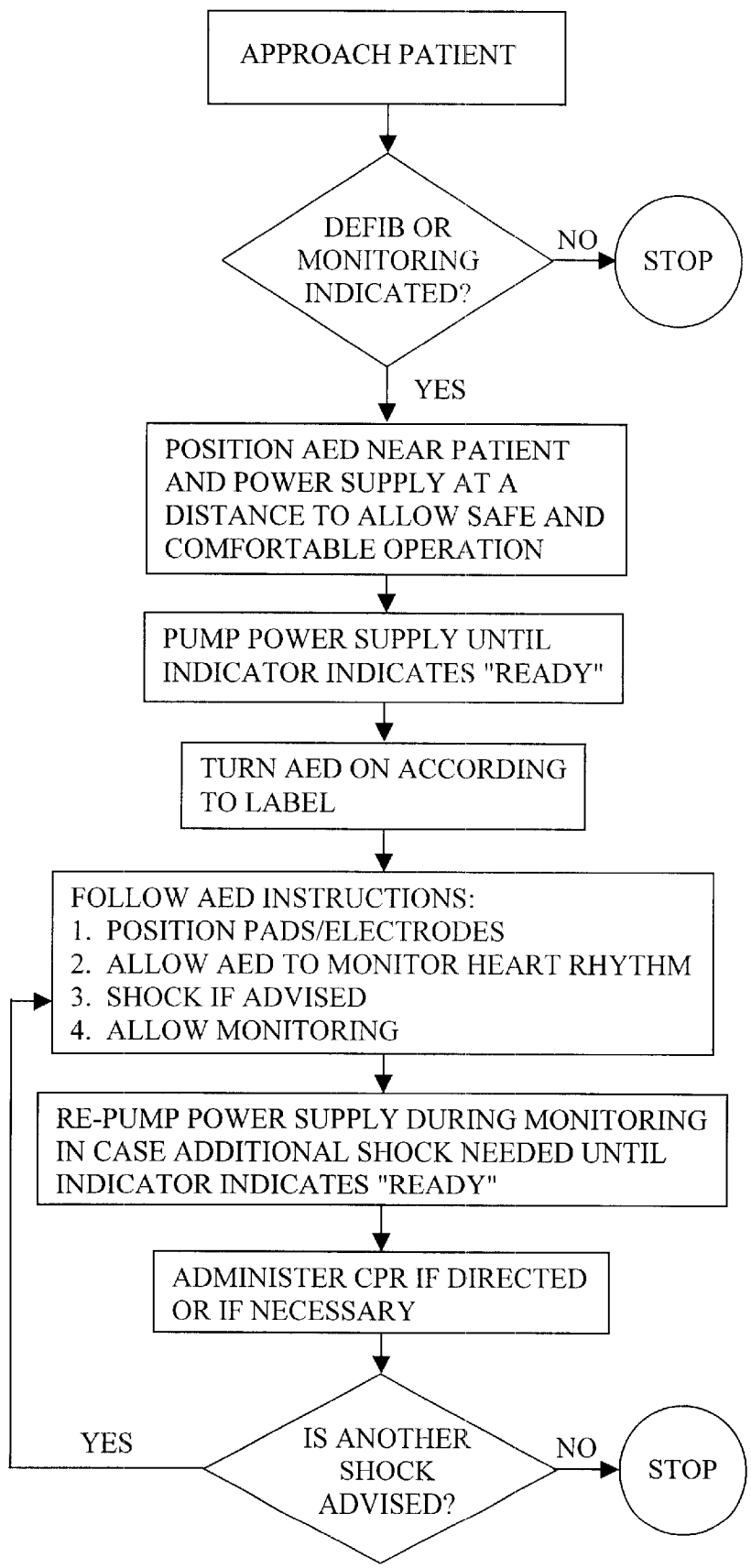
FIG. 5 represents a flow chart showing the method of operating the electrotherapy device according to the invention.

FIG. 5 illustrates a flow chart showing an embodiment of a method of operating a device according to the present invention. As shown in FIG. 5, a patient is approached. It is determined whether it appears that monitoring and/or defibrillation might be needed. This determination could be made through application of prior training or through labeling on an AED or spoken commands emanating from the AED. If monitoring and/or defibrillation do not appear to be needed, then the process is stopped. Otherwise, the process proceeds to the next step.

If monitoring and/or defibrillation appear to be needed, then an AED may be positioned in the vicinity of the patient. The power supply may be positioned at any distance from the patient that permits safe, comfortable, and/or safe operation of the AED and power supply. At this point, it may be necessary to connect the power supply to the AED. Along these lines, a pedal or other member may be stored in a folded and/or retracted position and require deployment and positioning.

The power supply may then be operated as described herein. The power supply may be operated, such as by depressing a pedal, until an indicator, if included in the device, indicates that the power supply is ready for use. At this point, the AED may be turned on. The AED may include a power switch for this purpose.

Electrodes may then be attached to the patient. The AED may then monitor the patient's heart rhythm. If the AED detects a shockable rhythm, then the AED will indicate that a defibrillating shock is needed. The defibrillating shock may then be administered. The patient's heart rhythm will then be monitored.

If additional shock is needed, the power supply may be pumped again. If necessary, cardiopulmonary resuscitation may be administered if directed by the AED instructions. It is determined whether another shock is necessary. If so, then the shock is delivered, if not, then the process is terminated.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments

What is claimed is:

1. A defibrillator device, comprising:
   a human powered power supply;
   an energy delivery system operably connected to the power supply for delivering a defibrillation shock to a patient;
   a controller operably connected to the energy delivery system for controlling the energy delivery system; and
   a patient monitor operably connected to the controller for monitoring the patient's heart rhythm.

2. The device according to claim 1, wherein the energy delivery system comprises a pair of electrodes operably connected to the energy delivery system for delivering the electric energy to the patient.

3. The device according to claim 1, further comprising:
   a patient monitor operably connected to the controller for monitoring the patient.

4. The device according to claim 3, wherein the device is a defibrillator and the monitor monitors a patient's heart rhythm.

5. The device according to claim 1, further comprising a a human operated pedal for powering the power supply.

6. The device according to claim 5, further comprising:
   a foot pedal for powering the power supply.

7. The device according to claim 5, further comprising:
   a hand-actuated member for powering the power supply.

8. The device according to claim 1, further comprising:
   a foot pedal for powering the power supply.

9. The device according to claim 1, further comprising:
   a hand-actuated member for powering the power supply.

10. The device according to claim 1, wherein the electrotherapy device comprises a defibrillator, a cardioverter, or a training device.

11. The device according to claim 1, wherein the power supply is physically separated from the energy delivery system.

12. The device according to claim 1, further comprising:
    a super capacitor for storing energy generated by the power supply.

13. The device according to claim 1, further comprising:
    a battery for storing energy generated by the power supply.

14. An electrotherapy device, comprising:
    a human powered power supply;
    an energy delivery system operably connected to the power supply for delivering an electric energy to a patient;
    a controller operably connected to the energy delivery system for controlling the energy delivery system,
    and a human operated pedal for powering the power supply.

15. A defibrillator device, comprising:
    a human powered power supply;
    an energy delivery system operably connected to the power supply for delivering a defibrillation shock to a patient; and
    a controller operably connected to the energy delivery system for controlling the energy delivery system.

16. An electrotherapy device, comprising:
    a human powered power supply;
    an energy delivery system operably connected to the power supply for delivering an electric energy to a patient;
    a controller operably connected to the energy delivery system for controlling the energy delivery system; and
    a foot pedal for powering the power supply.

17. An electrotherapy device, comprising:
    a human powered power supply;
    an energy delivery system operably connected to the power supply for delivering an electric energy to a patient;
    a controller operably connected to the energy delivery system for controlling the energy delivery system; and
    a hand-actuated member for powering the power supply.

18. An electrotherapy device, comprising:
    a human powered power supply;
    an energy delivery system operably connected to the power supply for delivering an electric energy to a patient;
    a controller operably connected to the energy delivery system for controlling the energy delivery system; and
    a super capacitor for storing energy generated by the power supply.

* * * * *